US00RE45510E

(19) United States
(12) Reissued Patent
Iwahashi et al.

(10) Patent Number: US RE45,510 E
(45) Date of Reissued Patent: May 5, 2015

(54) PATCH HAVING EASILY DETACHABLE RELEASE SHEET

(75) Inventors: Hideaki Iwahashi, Saga (JP); Shigeo Ota, Tokyo (JP); Nobuo Tsutsumi, Tokyo (JP); Takafumi Miyachika, Saga (JP)

(73) Assignee: Hisamitsu Pharmaceutical Co., Inc., Saga (JP)

(21) Appl. No.: 13/687,376

(22) Filed: Nov. 28, 2012

Related U.S. Patent Documents

Reissue of:
(64) Patent No.: 7,910,792
Issued: Mar. 22, 2011
Appl. No.: 12/063,688
PCT Filed: Aug. 17, 2006
PCT No.: PCT/JP2006/316180
§ 371 (c)(1),
(2), (4) Date: Feb. 13, 2008
PCT Pub. No.: WO2007/020980
PCT Pub. Date: Feb. 22, 2007

(30) Foreign Application Priority Data

Aug. 17, 2005 (JP) ..... 2005-236748

(51) Int. Cl.
*A61F 13/00* (2006.01)

(52) U.S. Cl.
CPC ..... *A61F 13/00029* (2013.01)

(58) Field of Classification Search
USPC ..... 602/41–54; 128/889–890
See application file for complete search history.

(56) References Cited

U.S. PATENT DOCUMENTS

| | | | | |
|---|---|---|---|---|
| 2,477,960 | A | 8/1949 | Caldwell | |
| D157,709 | S | 3/1950 | Smith | |
| 2,613,696 | A | 10/1952 | MacIntyre | |
| 2,877,765 | A * | 3/1959 | Bunyan | 602/47 |
| 3,399,672 | A * | 9/1968 | Gardner et al. | 602/51 |
| 4,537,809 | A | 8/1985 | Ang et al. | 428/41 |
| 4,587,146 | A | 5/1986 | Anhäuser et al. | 428/41 |
| 5,052,381 | A * | 10/1991 | Gilbert et al. | 602/52 |
| 5,266,371 | A | 11/1993 | Sugii et al. | 428/40 |
| D369,907 | S | 5/1996 | Sayovitz et al. | D5/53 |
| D370,127 | S | 5/1996 | Bonaddio et al. | D5/58 |
| D389,581 | S | 1/1998 | Fein | D24/189 |
| 5,998,694 | A | 12/1999 | Jensen et al. | 602/57 |
| D477,086 | S | 7/2003 | Tsuruda et al. | D24/189 |
| D605,299 | S | 12/2009 | Iwahashi et al. | D24/189 |
| D625,017 | S | 10/2010 | Iwahashi et al. | D24/189 |

FOREIGN PATENT DOCUMENTS

| | | | |
|---|---|---|---|
| EP | 1181930 | A1 | 2/2002 |
| EP | 1293199 | A1 * | 3/2003 |
| JP | 50-123187 | | 10/1975 |
| JP | 50-133797 | | 11/1975 |

(Continued)

OTHER PUBLICATIONS

Notice of Allowance and Search Report from TW 095130321, Aug. 17, 2006.

*Primary Examiner* — Michael A. Brown
(74) *Attorney, Agent, or Firm* — Licata & Tyrrell P.C.

(57) ABSTRACT

A patch permitting division of only its release sheet by simply pulling right and left, wherein detachment of the release sheet is easy. There is provided a patch comprising a stretchable support, a plaster applied substantially all over one major surface of the support and a release sheet attached to the whole surface of the plaster wherein only the release sheet is divided at a division zone by simply pulling right and left, and wherein one or two or more precut parts that open when the patch is pulled right and left are disposed in the neighborhood on the division zone.

11 Claims, 17 Drawing Sheets

(56) References Cited

FOREIGN PATENT DOCUMENTS

| | | |
|---|---|---|
| JP | 1-165023 | 11/1989 |
| JP | 4-92220 | 8/1992 |
| JP | 05-38348 | 2/1993 |
| JP | 5-54515 | 7/1993 |
| JP | 6-17722 | 3/1994 |
| JP | 7-500751 | 1/1995 |
| JP | 7-40744 | 7/1995 |
| JP | D951213 | 4/1996 |
| JP | 08-112305 | 7/1996 |
| JP | 08-280734 | 10/1996 |
| JP | D980089 | 4/1997 |
| JP | D980090 | 4/1997 |
| JP | D951213/1 | 4/1999 |
| JP | D980089/1 | 4/1999 |
| JP | D980090/1 | 4/1999 |
| JP | D980089/2 | 1/2000 |
| JP | D980090/2 | 1/2000 |
| JP | D951213/2 | 3/2000 |
| JP | D980089/3 | 3/2000 |
| JP | D980089/4 | 3/2000 |
| JP | D980089/5 | 3/2000 |
| JP | D980089/6 | 3/2000 |
| JP | D980090/3 | 3/2000 |
| JP | D980090/4 | 3/2000 |
| JP | D980090/5 | 3/2000 |
| JP | D980090/6 | 3/2000 |
| JP | 2001-335471 | 12/2001 |
| JP | 2002-345881 | 12/2002 |
| JP | 2005-192619 | 7/2005 |
| JP | 2006-130085 | 5/2006 |
| JP | D1286135 | 11/2006 |
| JP | D1286136 | 11/2006 |
| JP | D1294853 | 2/2007 |
| JP | D1294854 | 2/2007 |
| JP | D1294855 | 2/2007 |
| JP | D1294856 | 2/2007 |
| JP | D1294915 | 2/2007 |
| JP | D1295224 | 2/2007 |
| JP | D1295225 | 2/2007 |
| JP | D1295226 | 2/2007 |
| JP | D1295227 | 2/2007 |
| JP | D1296080 | 3/2007 |
| JP | D1296081 | 3/2007 |
| JP | D1296190 | 3/2007 |
| JP | D1296283 | 3/2007 |
| JP | D1296284 | 3/2007 |
| JP | D1296285 | 3/2007 |
| JP | D1296286 | 3/2007 |
| JP | D1297173 | 3/2007 |
| JP | D1297174 | 3/2007 |
| TW | 532145 | 5/2003 |
| WO | WO 93/08777 | 5/1993 |

* cited by examiner

PATCH HAVING EASILY DETACHABLE RELEASE SHEET

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This patent application is the National Stage of International Application No. PCT/JP2006/316180 filed Aug. 17, 2006, which claims the benefit of priority from Japanese Application No. 2005-236748 filed Aug. 17, 2005, teachings of each of which are herein incorporated by reference in their entirety.

TECHNICAL FIELD

The invention relates to a patch such as a cataplasm or a plaster. More particularly, it relates to a patch that is excellent in convenience, wherein the patch can be applied on a diseased part cleanly and simply even by an aged person without unnecessarily touching its adhesive surface and without leaving creases on the patch such as the cataplasm or the plaster.

BACKGROUND ART

In recent years, as an aging population grows and as a result of computer uses for rationalization of office work, more people tend to complain aches in the lower back, the shoulder, the knee, the elbow, and the like; thus a compress, a plaster or the like are widely used as a control medicine. In general, while a patch such as a compress or an adhesive mass has a structure in which a support, an adhesive mass and a release sheet are laminated, it is difficult to remove the release sheet when use, and in particular, this is the problem particularly for frequent users, i.e. aged persons.

In order to solve this problem, for example, a patch, wherein a release sheet can easily be detached by forming with two pieces of release sheets put together at the central part of the patch and bent from the joint and by providing a pull tab part (Patent document 1), and a patch, wherein a release sheet can easily be detached by providing a cutting line in a shape such as a wavy pattern or a zigzag pattern having a convex part and a concave part in the release sheet and by bending the entire patch, whereby said convex part becomes a catching part (Patent document 2) are known. However, it is costly to form the pull-tab part on the former patch, and it is necessary to handle the patch with care because the formed pull-tab may be hooked. In addition, the latter patch required a certain level of rigidity so that the release sheet is detached when bending the patch, and therefore, accompanied a certain restriction in a material of the release sheet.

In the meantime, a first-aid adhesive plaster is known in a field of an adhesive plaster having a sterile pad, wherein a piece of a thin plate for detachment having a cutting with a wavy line, is used and divided into two pieces by pulling apart (Patent document 3). However, to detach the divided thin plate for detachment, actions such as bending the first-aid adhesive plaster itself and shifting it from one hand to the other are needed, and therefore, it does not always exhibit excellent usability (easiness for application) (Patent document 3).

Further, a patch excellent in usability (easiness for application) is known in a field of a patch, in which only a release sheet can be divided by simply pulling apart (Patent document 4), however, since the needs of consumers, who are mainly aged persons and who seek superior usability (easiness for application), it is desired to provide an advanced patch with a simpler operation to detach the release sheet.

Patent document 1: JP, A, 7-500751
Patent document 2: JP, U, 1-165023
Patent document 3: JP, U, 50-133797
Patent document 4: JP, A, 8-112305

DISCLOSURE OF THE INVENTION

Problems to Be Solved by the Invention

Consequently, it is an object of the present invention to provide a patch, in which only its release sheet is divided by pulling apart, while having superior usability (easiness for application) and simpler operation to detach the release sheet.

Means to Solve the Problems

To solve the above problems, the inventors have found that, by providing one or more precut parts near the division zone on a release sheet that are opened when a patch is pulled apart, the divided release sheet is turned up cleanly; and the inventors further advanced the research, and completed the invention.

Namely, the invention relates to a patch comprising a stretchable support, an adhesive mass laminated substantially all over one surface of the support and a release sheet attached to the entire surface of the adhesive mass wherein only the release sheet is divided at a division zone by simply pulling apart, and wherein one or more precut parts that are opened when the patch is pulled apart are provided near the division zone.

Further, the invention relates to the patch, wherein the division zone is arranged in an S-shaped pattern, a wavy pattern or a zigzag pattern.

In addition, the invention relates to the patch, wherein the division zone is arranged in a straight-line pattern.

Further, the invention relates to the patch, wherein the [division zone is arranged in] *precut parts are provided in the form of* a T-shaped pattern.

In addition, the invention relates to the patch, wherein the longitudinal bar of a T-shape is parallel to pulling directions of the patch and the tip of said longitudinal bar is pointed toward the division zone.

Further, the invention relates to the patch, wherein the precut part is provided convexly toward the pulling directions from the division zone.

In addition, the invention relates to the patch, wherein the [division zone is arranged in] *precut parts are provided in the form of* a V-shaped pattern or a circular arc pattern.

Further, the invention relates to the patch, wherein the release sheet is one piece of release sheet having a division zone, and only the release sheet is divided at the division zone due to the difference in a rate of elongation between the release sheet and the support by simply pulling the patch apart.

Effect of the Invention

In the invention, by adopting the above constitution, not only a release sheet is divided by simply pulling a patch apart without starting from a detachment step such as searching edges of the release sheet or a support, but the release sheet can also be picked extremely easily because the edges of the divided parts of the release sheet are favorably turned up with the presence of a precut part. Furthermore, since a part of an adhesive mass is exposed more widely as a result of a favorable turn-up, application of the patch becomes easier without shifting the patch from one hand to the other (so-called one-touch operation) by directly applying an exposed part of the adhesive mass, which is exposed more widely, to a diseased part.

Further, by clearly illustrating on a release sheet and/or a support How To Use, i.e. how to pull a patch apart and how to stick on a diseased part in one-touch without shifting from one hand to the other, usability (sticking easiness) of the patch can further be improved, and it is possible to make the patch more advanced.

As for a good turn-up of a release sheet when pulling a patch of the invention apart, it is considered that first, the release sheet is divided at a division zone; simultaneously, an opening is formed at a precut part; air enters into a space between the release sheet and an adhesive mass from the precut part, and this air facilitates a turn-up.

In addition, in case of pulling a patch apart, when a precut part is provided convexly toward the pulling directions, not only an adhesive mass is exposed more widely, but the tip of the convex pattern is also caught by the adhesive mass; therefore, a turn-up state of the release sheet can be maintained even if a lateral tension is loosened. As a result, a turn-up part of the release sheet does not stick to the adhesive mass again and can easily be picked.

DESCRIPTION OF SYMBOLS

Figure 1:
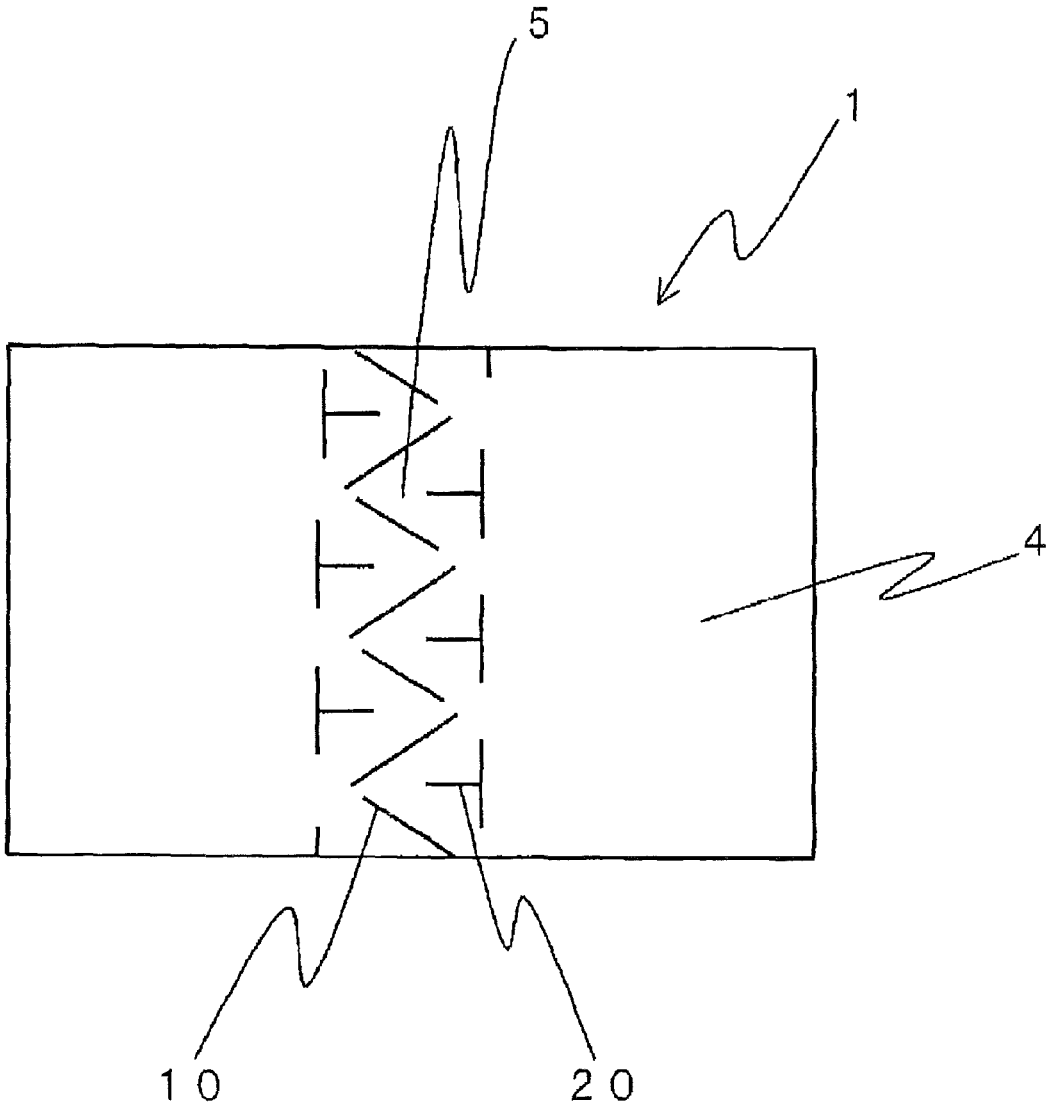
FIG. 1 shows a descriptive drawing (front view) illustrating one embodiment of a patch of the invention.

1 Patch
2 Support
3 Adhesive mass
4 Release sheet
5 Section
10 Division zone
20 Precut part

BEST MODE FOR CARRYING OUT THE INVENTION

A division zone according to the invention is a part where a release sheet is divided when pulling a patch apart. This may be located at a desired position such as substantially central part of the release sheet or its peripheral part. The division zone of the invention typically includes a thin cut part thinned without penetrating the release sheet, which is so-called a half-cut, a perforation cut part in which the release sheet is cut at a designated interval, the other called as a weakened line or the like, further, a mortise (notch) formed on the side of the release sheet in an I-shaped pattern, a V-shaped pattern and the like. In this case, the release sheet is one piece of release sheet having a division zone, and by simply pulling apart only the release sheet is divided at said division zone due to the difference in a rate of elongation. Further, according to one embodiment of the invention the release sheet consists of two pieces of completely divided release sheets, however, the release sheet is preferably one piece of release sheet having the division zone from viewpoints such as protection of the patch shape, prevention from vaporization of an efficacious ingredient, and the like.

In case of the division zone in the form of a thin cut part or a cut part in a perforation pattern, it is formed across the release sheet at substantially central part, a peripheral part or the like so that the release sheet is divided, and the form of said division zone may be arranged in a pattern such as a straight pattern, an S-shaped pattern, a wavy pattern or a zigzag pattern, and further, for example, entire division zone may be arranged in a zigzag pattern, wherein each line of said zigzag may further form a zigzag-pattern, a wavy pattern or the like, or a combination of the above patterns, and may be arranged in any other patterns. In particular, the S-shaped pattern, the wavy pattern, the zigzag pattern or the like which form a convex part and a concave part are preferable. When the distance (stroke) between one convex part and its neighboring convex part is relatively long (in a case of a small number of strokes), a section formed after division of the release sheet is large and can easily be picked.

The precut part according to the invention is, without limitation, provided in a form which is opened when the patch is pulled, and this open part contributes to the turn-up of the release sheet; typically, in the form of a straight pattern, a T-shaped pattern, a V-shaped pattern, a folding-fan pattern or the like. In particular, it is preferable that the longitudinal bar of a T-shape is parallel to the pulling directions of the patch and the tip of said longitudinal bar is pointed toward a division zone and/or is provided convexly toward the pulling directions from a division zone.

One or more precut part are provided near the division zone, and preferably are in a closed state before use. It may be provided in any pattern as long as it is opened when pulling the patch apart, and typically, a precut penetrating the release sheet, a thin cut part of a half-cut pattern, a perforation cut part and the like.

Particularly, it is preferred to provide the precut part convexly toward the pulling directions from the division zone, because it promotes turn-up of the release sheet and prevent re-sticking of the release sheet; in particular, a V-shaped pattern or a circular arc pattern is preferable.

The patch according to the invention comprises the support, adhesive mass and release sheet, and those conventionally used can be used as described below.

Namely, as the release sheet for the patch according to the invention, a plastic film, which may be colorless or colored, such as a casted polypropylene (CPP), an oriented polypropylene (OPP), polyethylene terephthalate (PET), polybutylene terephthalate (PBT), polyethylene, polyester, polyurethane, polyvinyl chloride or polystyrene, silicone-treated treatment papers, which is a silicone-treated synthetic resin, synthetic paper, synthetic fiber or the like, aluminum foil, laminated paper, which is a kraft paper laminated with polyethylene or the like may be used.

The thickness of the above release sheet is in the range of 10 μm-75 μm, preferably 12 μm-40 μm, more preferably 15 μm-35 μm. If the release sheet is too thin, the release sheet tends to be intertwined with an adhesive mass when detached, and it is difficult to pick the release sheet because the release sheet is thin and slippery, further, the release sheet is easily divided when manufacturing, which results in lower workability or the like; the release sheet is easily creased when attaching the release sheet on the adhesive mass. On the other hand, if the release sheet is too thick, the release sheet can easily be picked for detachment, however it becomes difficult to divide as well as to cut an original sheet when manufacturing, and it tends to lower workability, etc.

The tensile strength of the release sheet is in the range of 10 g/cm-140 g/cm, preferably 20 g/cm-100 g/cm, more preferably 30 g/cm-60 g/cm. If the tensile strength of the release sheet is too small, the release sheet is cut on the way when manufacturing and can not continuously be attached on the adhesive mass; the release sheet is easily divided when placing a patch such as a cataplasm, a plaster or the like in a package bag; further a yield tends to be decreased. In addition, if the tensile strength of the release sheet is too large, it becomes difficult to divide the release sheet, and usability tends to be worsened.

The tensile strength can be measured using, for example, a tensile test machine AGS-100B (manufactured by Shimadzu Corporation) in terms of a weight at the time of rupture, wherein the release sheet is held by a chuck of 50 mm width with the standard point distance of 100 mm and pulled at 100 mm/min.

The release sheet having the thickness of 10 μm-75 μm and the tensile strength 10 g/cm-140 g/cm is particularly preferable, because in addition to the above workability and usability, the turn-up becomes more favorable together with elasticity of the release sheet and effects of the precut part provided in the release sheet, whereby the adhesive mass can be exposed more widely.

In addition, in order to clearly illustrate a detachment procedure, an indication such as a figure including an arrow or the like, a letter, a symbol, or the like may be drawn on both parts of the release sheet, or, for example, it may be colored. By such indication, coloring or the like, for example, by clearly indicating on the release sheet, a procedure how to pull the patch apart and how to stick on a diseased part in one-touch without shifting from one hand to the other, it is possible to use the patch while reading How To Use, and usability (sticking easiness) can be improved more. The above indication may be located on the support.

The release sheet may further be embossed, and typically, the entire surface or a partial area of the release sheet, for example, an area where can easily be picked by the hand for tearing the division zone, an area where it can easily be picked for detaching the release sheet which is torn, or the like, is embossed. A form of the embossing is not limited, as long as the release sheet can easily be picked by the hand without slipping; it may be formed, for example, in a lattice pattern, a circle pattern, an angular pattern, a star pattern, or the like, or in any other patterns.

The embossed release sheet has partially different strength, and therefore, promotes the turn-up; further, if the cut part is provided, ruggedness of the embossing and the cut part together give a favorable, variable turn-up; an adhesive mass surface becomes more exposed, resulting in further improvement in convenience when picking the release sheet. Further, owing to the turn-up that is not planar, there is a merit that the release sheet hardly sticks again to the adhesive mass.

As the support for the patch of the invention, it may be any support that is not divided when the release sheet is divided by pulling the patch apart. In addition, in case one piece of release sheet having a division part is used as the release sheet, there should be the difference in a rate of elongation between the release sheet and the above support so that only the release sheet is divided at division part when pulling said patch apart, while for a favorable turn-up of the release sheet when dividing, the difference is preferably not less than 0.3%.

As the support, examples are: stretch materials such as woven fabric, knitted fabric, non-woven fabric and non-woven paper. Specifically, natural fibers such as bast fibers like paper, cotton, hemp and jute, cellulose fibers such as vein fiber like Manila hemp, animal hair fibers like wool, and protein fibers like silk fiber and feather fiber, regenerated fibers such as regenerated cellulose fibers like rayon and cupra, and regenerated protein fiber, semi-synthetic fibers such as cellulose acetate and promix, nylon aramid fiber, polyethylene terephthalate fiber, polyester fiber, acryl fiber, polyolefin fibers like polyethylene and polypropylene, polyvinyl alcohol fiber, polyvinyl chloride fiber, polyvinylidene chloride fiber, polyvinyl chloride type fiber, polyurethane fiber, polyoxymethylene fiber, polytetrafluoroethylene fiber, polyparaphenylene benzbisthiazole (PBT) fiber, polyimide fiber, and the like may be used.

The above fibers are appropriately selected according to physical properties such as the thickness, stretching, tensile strength and workability, feeling when applying, covering for a diseased part, the transfer of a drug to the support, and the like.

The adhesive mass for the patch of the invention comprises a drug, which is contained in or disposed on a base, so that the patch such as a cataplasm and a plaster is effectively used. The adhesive mass is formed to hold water for sufficiently efficacious effects to the skin, while also to have adhesiveness and appropriate cohesiveness without giving excessive softness at an ambient temperature or higher and without leaving the adhesive mass on the skin.

In addition, the adhesive mass is prepared from a thickener, a moistening agent and the like, while as the thickener, it is desirable to be able to stably hold water in 30%-80% and to have a water-holding property. As specific examples, aqueous polymers including natural polymers such as those of plant origins like guar gum, locust bean gum, carrageenan, alginic acid, sodium alginate, agar, gum arabic, tragacanth gum, karaya gum, pectin and starch, those of microorganism origins like xanthan gum and acacia gum, and those of animal origins like gelatin and collagen, semi-synthetic polymers such as celluloses like methyl cellulose, ethyl cellulose, hydroxyethyl cellulose and sodium carboxymethyl cellulose, and starches like soluble starch, carboxymethyl starch and dialdehyde starch, synthetic polymers such as vinyls like polyvinyl alcohol, polyvinyl pyrrolidone and polyvinyl methacrylate, acrylics like polyacrylic acid and sodium polyacrylate, further polyethylene oxide, methylvinylether-maleic anhydride copolymer, and the like may appropriately be used.

Sodium polyacrylate is particularly preferable because it has high gel strength and excellent in a water-holding property. Further, sodium polyacrylate of average polymerization degree 20000-70000 is preferable. If the average polymerization degree is smaller than 20000, a thickening effect is poor, and there is a tendency that a sufficient gel strength cannot be obtained. On the other hand, if the average polymerization degree is larger than 70000, the thickening effect is too strong, and workability tends to be reduced. In addition, by using a combination of two or more of the above aqueous polymers, for example, a polymer complex with a strong ionic polymer of sodium polyacrylate is formed, and an elastic gel with higher gel strength can be obtained.

As the moistening agent, polyvalent alcohols such as glycerin, propylene glycol and sorbitol, and as a filler, kaolin, talc, titanium, bentonite, aluminum silicate, titanium oxide, zinc oxide, aluminum metasilicate, calcium sulfate, calcium phosphate and the like may be added. In addition, as a solubilizer or an absorption enhancer, propylene carbonate, crotamiton, 1-menthol, mentha oil, limonene, diisopropyl adipate or the like, and as an adjuvant, methyl salicylate, glycol salicylate, 1-menthol, thymol, mentha oil, vanillic amide nonylate, red pepper extract and the like may be added. Further, if necessary, a stabilizing agent, an antioxidant, an emulsifying agent, and the like may be added.

In addition, if necessary, a cross-linking agent, a polymerizing agent and the like may be added, which can strengthen the adhesive mass as well as improve a water-holding property. The cross-linking agent and the polymerizing agent are appropriately selected according to types of the thickener and the like. For example, if polyacrylic acid or polyacrylate is selected as the thickener, a compound having at least two epoxy groups in the molecule, polyvalent metal compounds such as inorganic salts like a hydrochloride, sulfate, phosphate and carbonate and organic salts like a citrate, tartarate, gluconate and stearate of Ca, Mg, Al or the like, oxides like zinc oxide and silica, and hydroxides like aluminum hydroxide and magnesium hydroxide are preferably used. In addition, if polyvinyl alcohol is selected as the thickener, complexes of adipic acid, thioglycolic acid, an epoxy compound (epichlorhydrin), aldehydes, an N-methylol compound, and a compound of Al, Ti, Zr, Sn, V, Cu, B, Cr or the like are preferably used.

In addition, if polyvinyl pyrrolidone is selected as the thickener, methylvinyl ether-maleic anhydride copolymer, a polyacid compound or alkaline salts thereof (poly acrylic acid, tannic acid and derivatives thereof) and the like are preferably used. In addition, if polyethylene oxide is selected as the thickener, a peroxide, a polysulfone azide and the like are preferably used. In addition, if methylvinyl ether-maleic anhydride copolymer is selected as the thickener, a polyfunctional hydroxyl compound, polyamine, iodine, gelatin, polyvinyl pyrrolidone, iron, mercury and lead salts, and the like are preferably used. If gelatin is selected as the thickener, aldehydes such as formaldehyde, glutar aldehyde, dialdehyde starch and glyoxal, diepoxides such as butadiene oxide, diketones such as divinyl ketone, diisocyanates and the like are preferably used.

In addition, if sodium polyacrylate is selected as the thickener, polyvalent metal salts such as lithium hydroxide, zinc hydroxide, aluminum hydroxide, and sodium borate are preferably added as a cross-linking agent. In particular, the zinc salt and aluminum salt are preferable. A cross-linking reaction is accelerated. The concentration of the polyvalent metal salts added as the cross-linking agent is preferably 0.5-1.5 equivalent weight per 1 equivalent weight of the thickener (or the aqueous polymer). If the concentration of the polyvalent metal salt is too low, the reaction is too slow, and a gel strength tends to be lower; if the concentration of the polyvalent metal salt is too high, the reaction is too rapid and gelation tends to be inhomogeneous and to lower workability.

As the cataplasm, its skin contact is good; it increases a skin absorption of an efficacious ingredient; it contains water as much as possible; it takes away heat from the skin when water in the adhesive mass evaporates while this evaporation thus gives a refreshed feeling; a horny layer is hydrated by water molecules evaporating from the inner side to accelerate the absorption of a drug; it does not loose adhesive strength at or around an ambient temperature; it does not give pain when detaching and does not leave the adhesive mass; it is not sticky. For these reasons, the adhesive mass is preferably made as follows: the thickener is 5 wt. %-20 wt. %, preferably 10 wt. %-15 wt. %; the moistening agent is 5 wt. %-40 wt. %; the filler is 20 wt. % or less; water is 10 wt. %-80 wt. %; the solubilizer is 0 wt. %-8 wt. %; the drug is 5 wt. % or less, preferably 0.5 wt. %-5 wt. %.

In addition, for the plaster and the like, as the base, an acrylic copolymer, an A-B-A type block copolymer, alicyclic petroleum resin, or one having a softening agent is suitably used. Further, elastic agents with thermo-plasticity such as an A-B type block copolymer, polybutene, silicone rubber, natural rubber, styrene-butadiene copolymer, NBR polyisobutylene, polyalkyl acrylate and synthetic isoprene, tackifiers such as terpene resin, petroleum resin, rosin, hydrogenated rosin and rosin-hydrogenated rosin ester, adhesiveness- or holding-modifiers such as animal and plant oils like liquid paraffin, olive oil, soya oil, beef tallow, lard, etc., polybutene, liquid polyisobutylene, lower isoprene and wax, fillers such as titanium oxide, zinc oxide, aluminum metasilicate, calcium sulfate and calcium phosphate, and the like may be blended.

As the A-B-A type block copolymer, a block copolymer of monovinyl-substituted aromatic compound A and conjugated diolefin copolymer B are preferably used. Specific examples are: Califlex TR-1101, Califlex TR-1107, Califlex TR-1111 and the like which are manufactured by Shell Chemicals, Solprene 418, Solprene 311 and the like which are manufactured by Phillips Petroleum Company, while the mix amount is 10-40 weight parts in an adhesive mass composition, preferably 15-30 weight parts.

As a drug that can be contained in the patch of the invention, examples are, without limitation, at least one kind of non-steroidal anti-inflammatory agent selected from methyl salicylate, glycol salicylate, 1-menthol, red pepper extract, vanillic amide nonylate, mentha oil, diclofenac, ibuprofen, indometacin, ketoprofen, loxoprofen, sulindac, tolmetin, lobenzarit, penicillamine, fenbufen, flurbiprofen, naproxen, pranoprofen, tiaprofenic acid, suprofen, felbinac, ketololac, oxaprozin, etodolac, zaltoprofen, piroxicam, pentazocine, buprenorphine hydrochloride, butorphanol tartarate, etc., and ester derivatives thereof or salts thereof, steroidal anti-inflammatory agents such as prednisolone, dexamethasone, hydrocortisone, betamethasone, fluocinonide, fluocinolone acetonide, prednisolone valerate acetate, dexamethasone dipropionate, diflucortolone valerate, difluprednate, betamethasone valerate, hydrocortisone butylate, clobetasone butylate, betamethasone butylate, clobetasone propionate, dexamethasone succinate, prednisolone 21-(2E,6E) farnesylate, hydrocortisone valerate, diflorasone acetate, dexamethasone propionate, betamethasone dipropionate, amcinonide, dexamethasone valerate, halcinonide, budesonide and alclometasone propionate.

The drugs may be used in a combination of two or more kinds as needed. In addition, these drugs, if necessary, may be contained in or disposed on the adhesive mass as a compound which may be derived in an ester form, a compound which may be derived an amide form, a compound which may be derived in an acetal form, or in a form of medically acceptable inorganic or organic salts. The amount of the drug is appropriately selected according to the type, the use, etc. of patches such as the cataplasm, plaster and the like in order to be able to apply an efficacious predetermined amount to a diseased part when applying to a patient.

Further, it is possible to use the patch of the invention as a cold compress or the like, which contains no drug.

The patch of the invention is illustrated below in more detail with the drawings. The invention, however, is not limited to these drawings.

The patch of the invention is typically as shown in FIG. 1. The patch 1 comprises the stretchable support 2, the adhesive mass 3 laminated substantially all over one surface of the above support 2 and the release sheet 4 attached to the entire surface of the above adhesive mass 3, wherein only the above release sheet 4 is divided at the division zone 10 by simply pulling apart, and wherein plural precut parts 20 are provided near the above division zone 10. In the figure, the division zone 10 is arranged in the perforation zigzag pattern and is placed in substantially central part of the patch 1, whereby the number of strokes is 3.5. In addition, after dividing the release sheet 4, a part of the precut part 20 is hooked on a part that becomes the section 5. The precut part 20 is provided in the T-shaped pattern, whereby the longitudinal bar of said T-shape is parallel to the pulling directions (the lateral directions in FIG. 1) of the patch 1 and the tip of said longitudinal bar is pointed toward the division zone 10.

The release sheet 4 can be divided at the division zone 10 by holding both ends of the patch 1 and pulling the release sheet 4 apart together with the support 2. In addition, at this time, the precut part 20 formed near the division zone 10 is opened, while air enters into a space between the release sheet 4 and the adhesive mass 3 from said open part, so that this air facilitates detachment of the release sheet 4 from the adhesive mass 3. In addition, the precut part 20, which is torn, makes bending extremely easy. Further, as the adhesive mass 3 is exposed wider, the patch 1 is applied to a diseased part by applying this exposed adhesive mass 3 to the diseased part and picking the section 5 to detach the turned-up release sheet 4. This enables the adhesive mass 3 to be exposed more widely than that of the conventional patches, the release sheet 4 to easily be detached and the patch 1 to be applied to a diseased part, without unnecessarily touching the adhesive mass 3 and creasing the patch 1.

In addition, the patch of the invention includes various embodiments shown in FIGS. 2-8.

Figure 2:
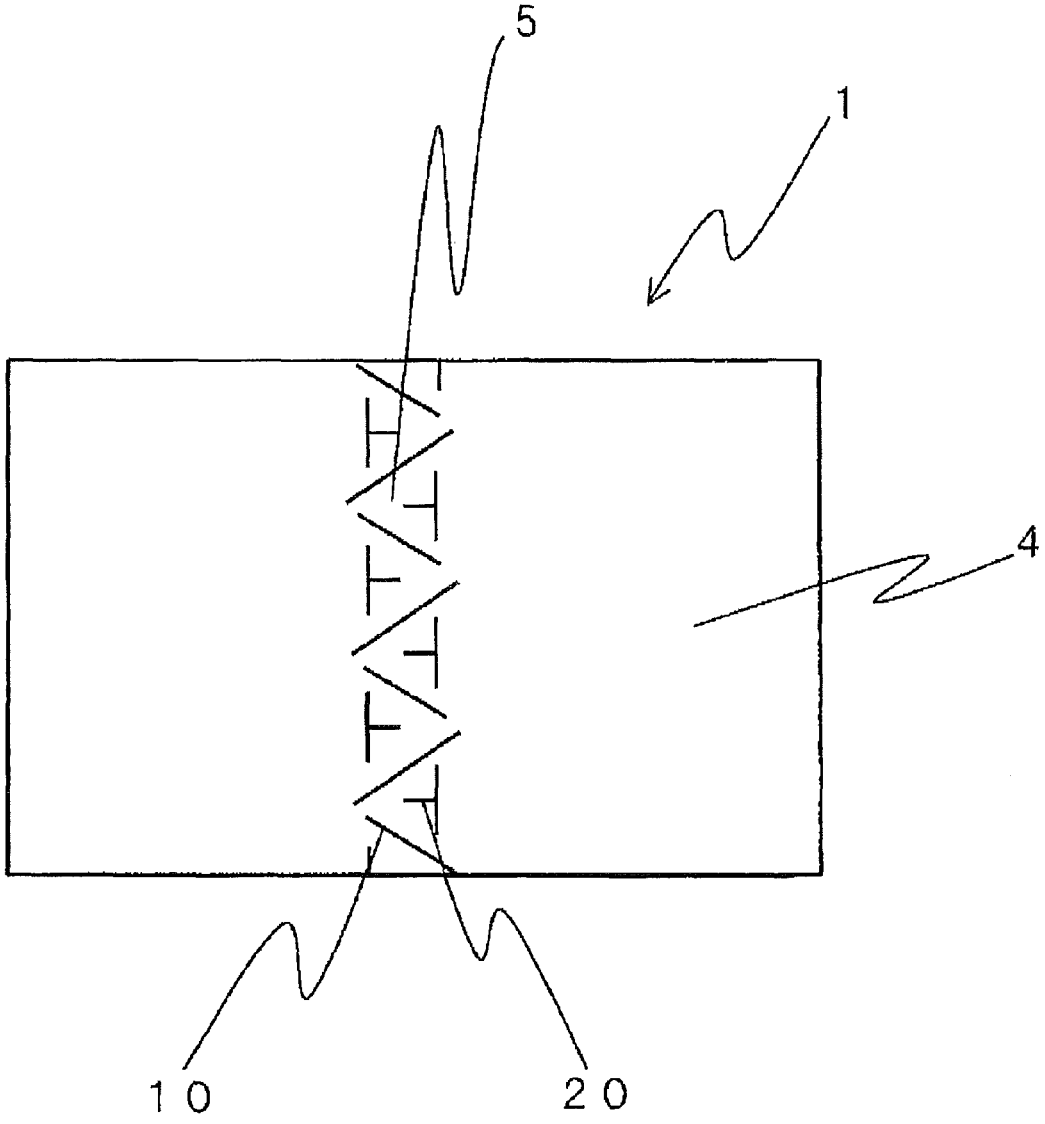
FIG. 2 shows a descriptive drawing (front view) illustrating one embodiment of a patch of the invention.

In FIG. 2, like the embodiment of FIG. 1, the T-shaped precut part 20 is provided such that the longitudinal bar of the T-shape is parallel to the pulling directions of the patch and the tip of said longitudinal bar is pointed toward the division zone; however, it is different in that one entire precut part 20 is provided inside (in the width between two tips of zigzag pattern) one section 5.

Figure 3:
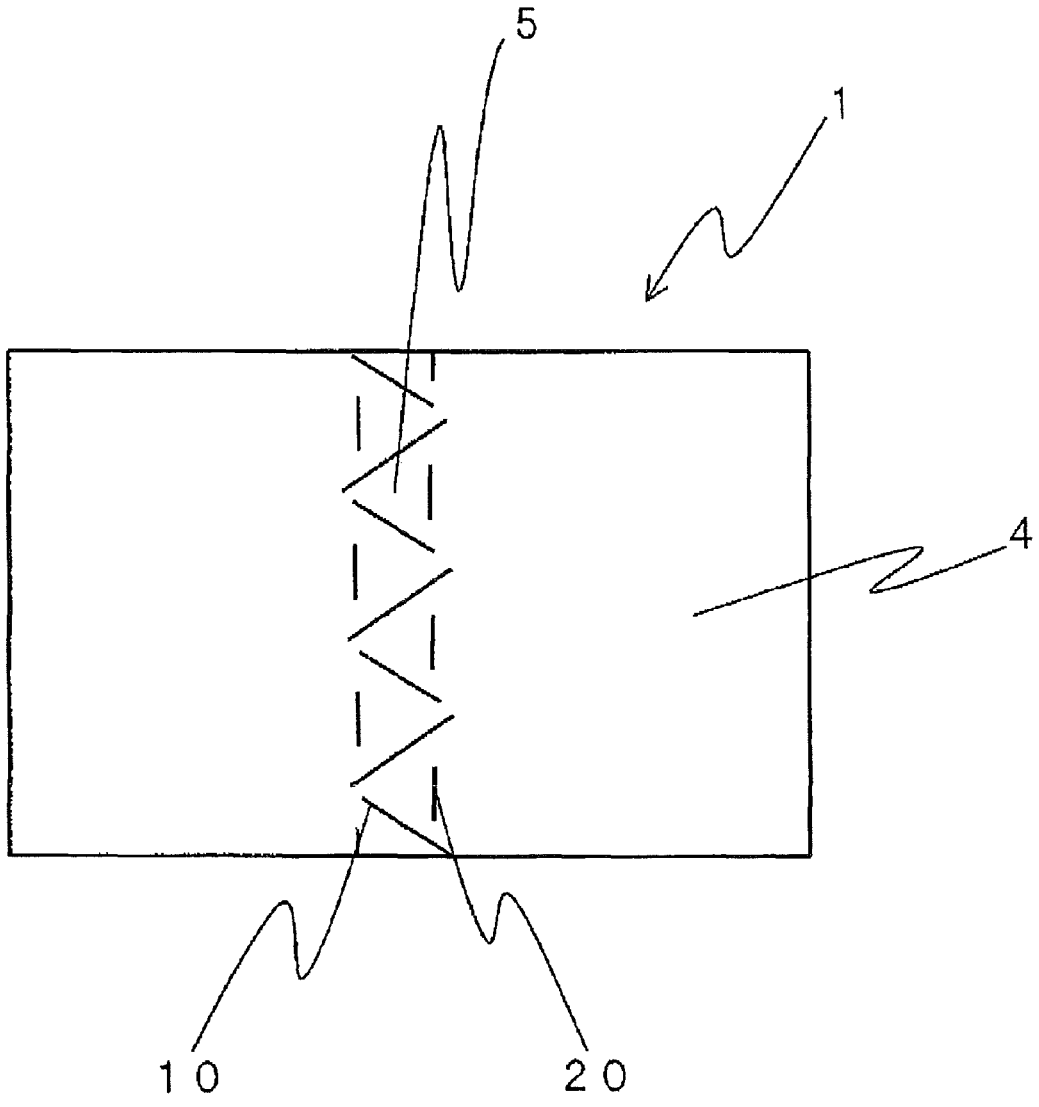
FIG. 3 shows a descriptive drawing (front view) illustrating one embodiment of a patch of the invention.

In FIG. 3, the straight precut part 20 is provided near the base of the triangle in the section 5, and is vertically provided in the pulling directions in the patch.

Figure 4:
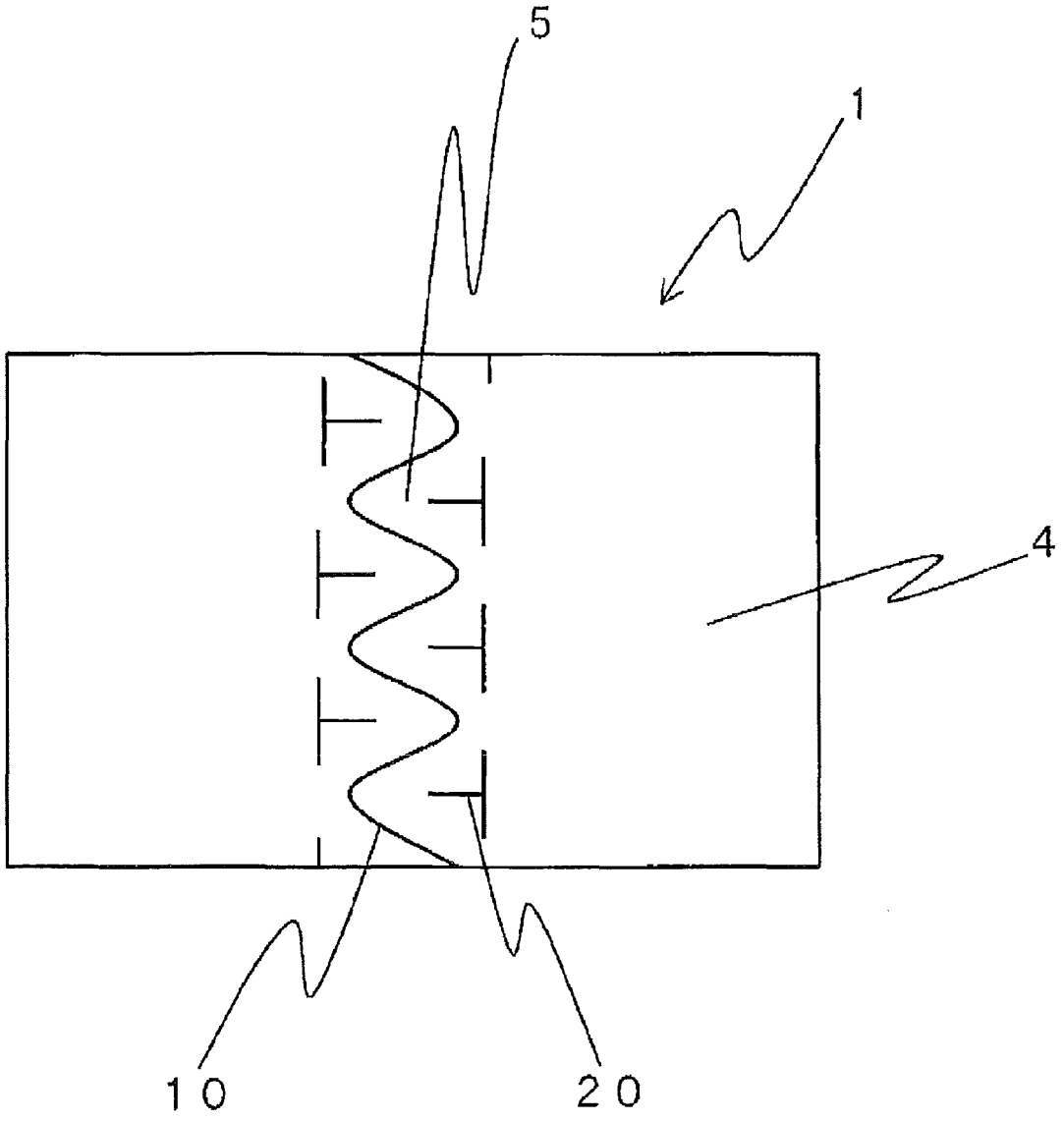
FIG. 4 shows a descriptive drawing (front view) illustrating one embodiment of a patch of the invention.

In FIG. 4, the division zone is arrange in the half-cut wavy pattern, and the precut part 20 of T-shaped pattern is provided in a similar way to that of FIG. 1.

Figure 5:
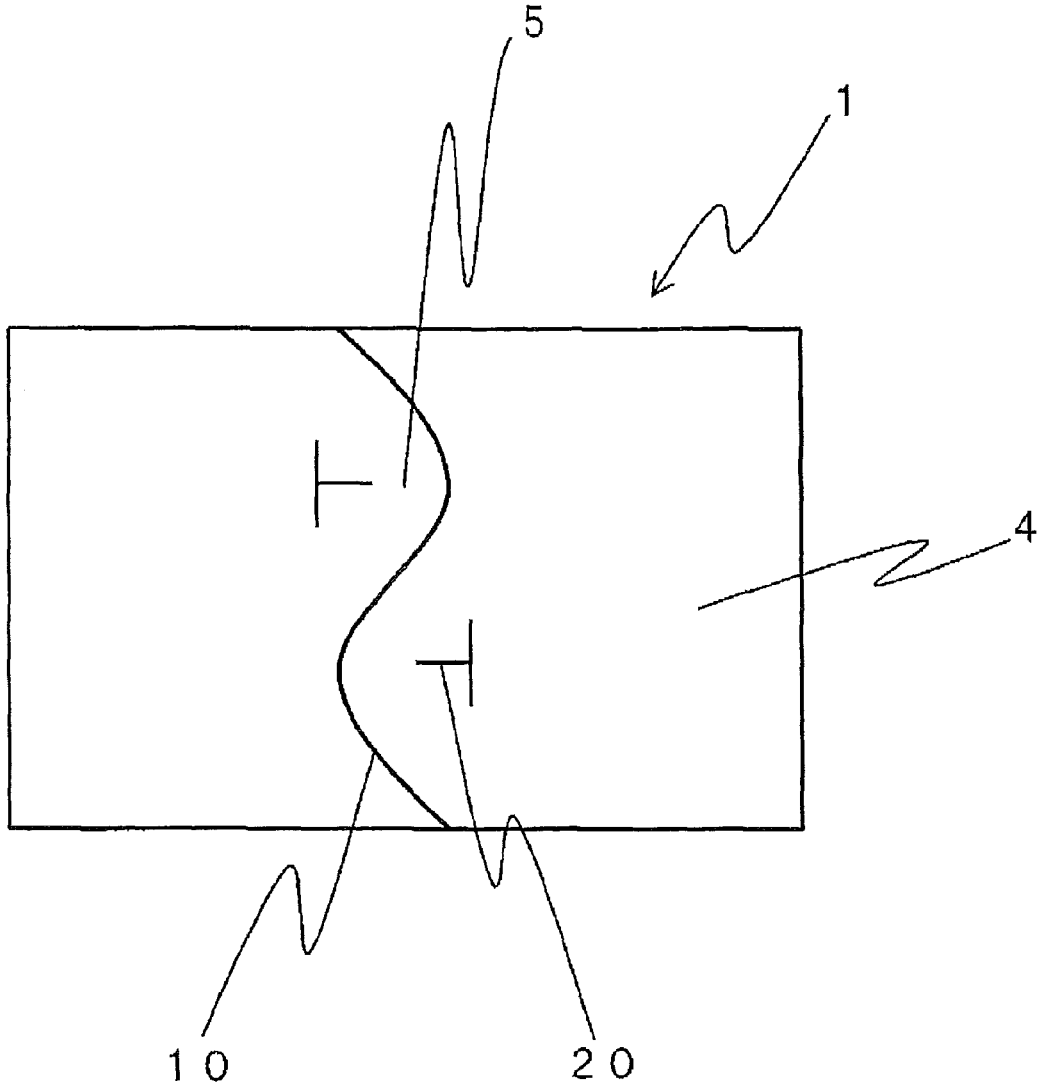
FIG. 5 shows a descriptive drawing (front view) illustrating one embodiment of a patch of the invention.
Figure 6:
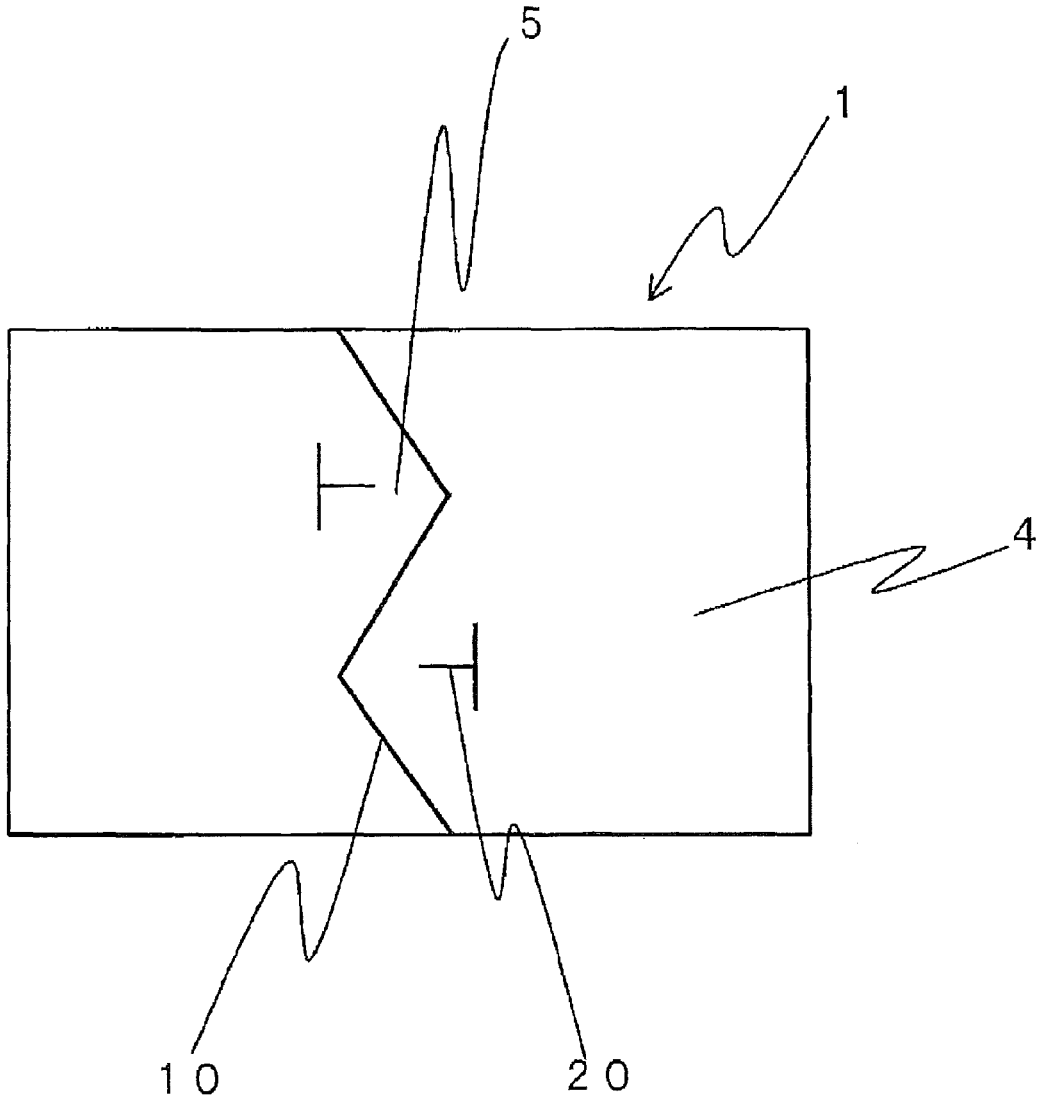
FIG. 6 shows a descriptive drawing (front view) illustrating one embodiment of a patch of the invention.

In FIGS. 5 and 6, the division zone is arranged in the half-cut S-shaped pattern (inverted S-shaped pattern) (FIG. 5) or zigzag pattern (FIG. 6), while the T-shaped precut part 20 is provided such that the longitudinal bar of the T-shape is parallel to the pulling directions of the patch and the tip of said longitudinal bar is pointed toward the division zone.

Figure 7:
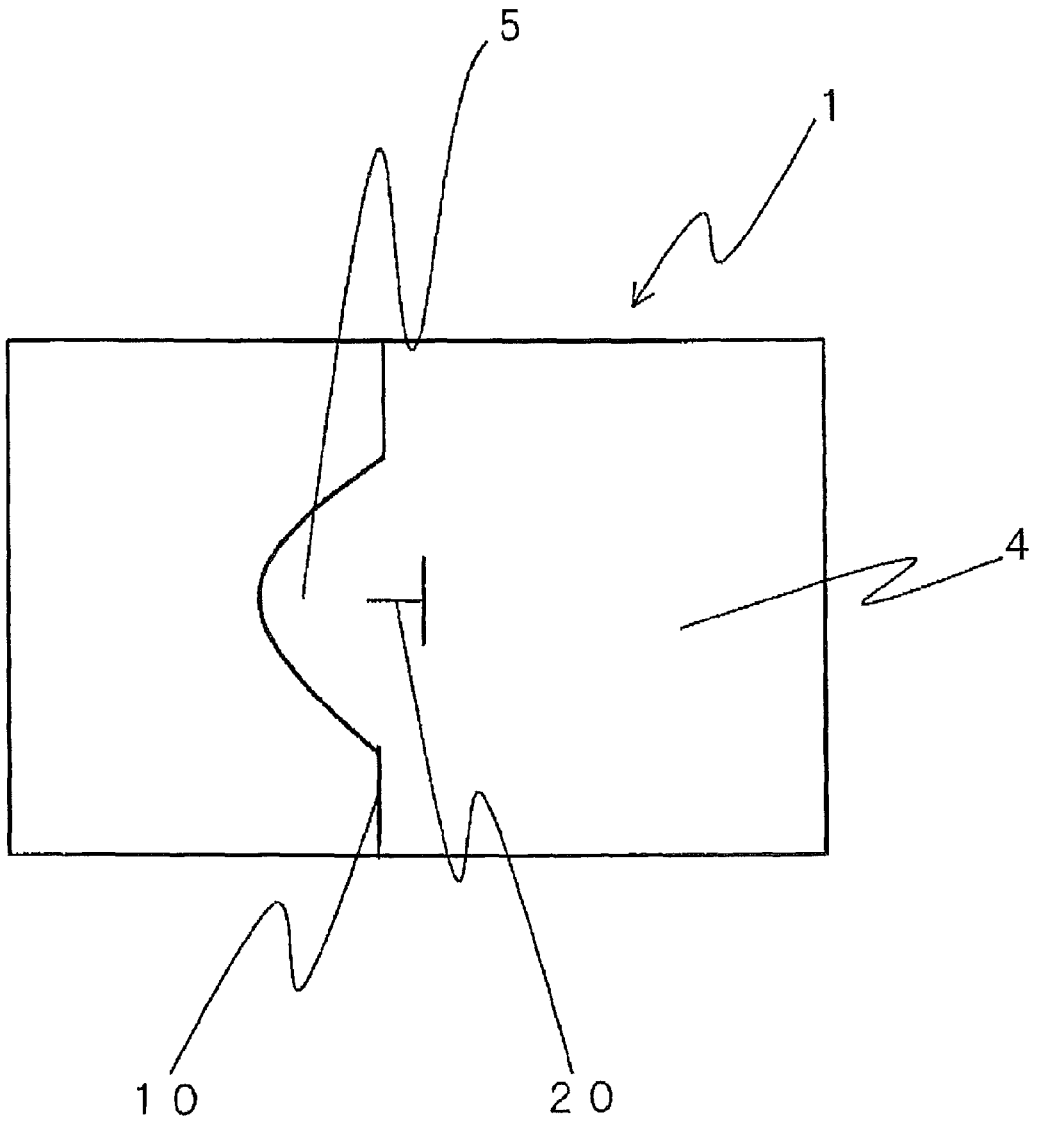
FIG. 7 shows a descriptive drawing (front view) illustrating one embodiment of a patch of the invention.

In FIG. 7, the division zone is arranged in the combination of the straight-line pattern and the curved line, and the T-shaped precut part 20 is provided.

Figure 8:
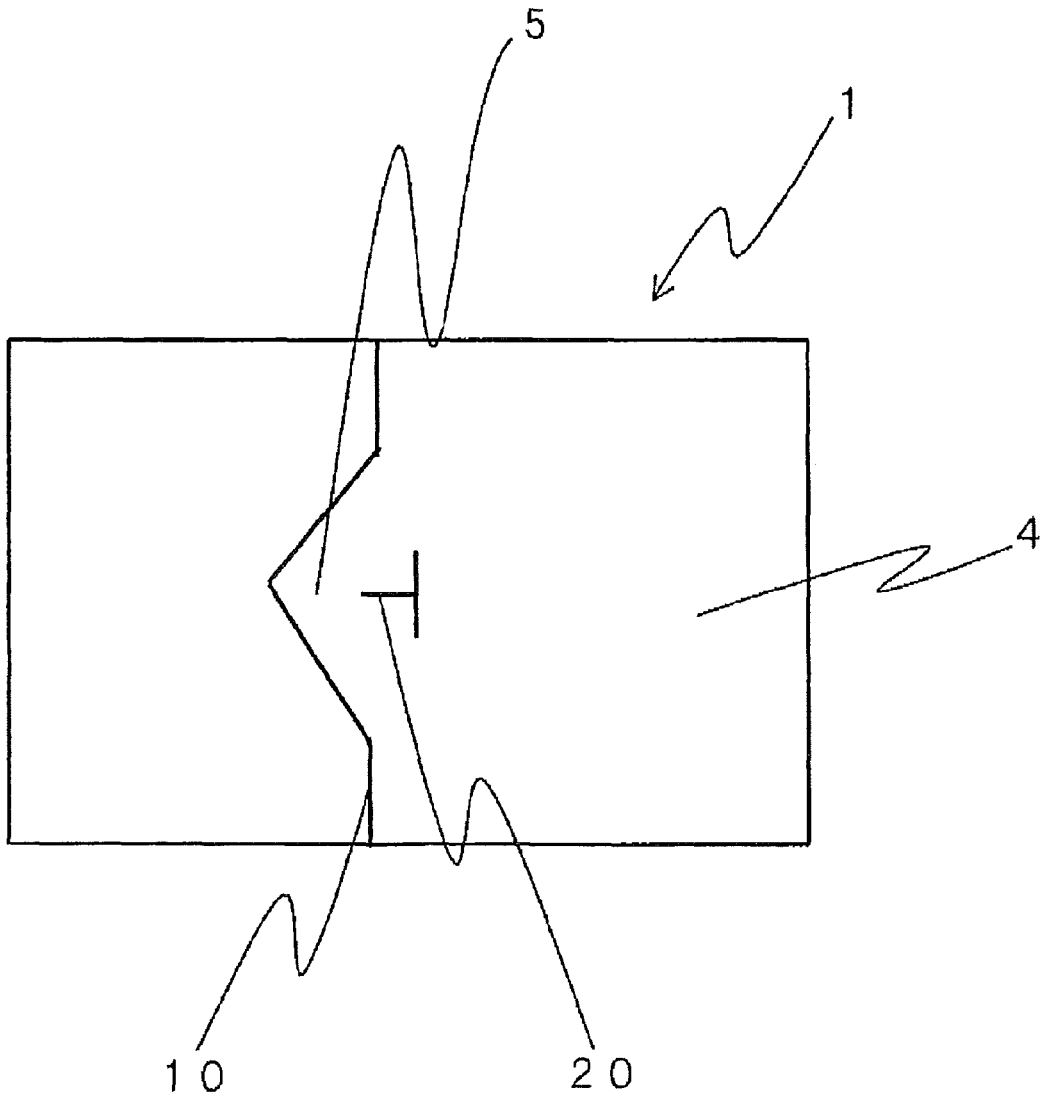
FIG. 8 shows a descriptive drawing (front view) illustrating one embodiment of a patch of the invention.

In FIG. 8, the division zone is arranged in the combination of the straight pattern and the zigzag pattern, and the T-shaped precut part 20 is provided.

In the patches shown in FIGS. 5-8, since the section 5 is formed relatively widely, the edges of the release sheet can easily be picked when detaching the release sheet.

Figure 9:
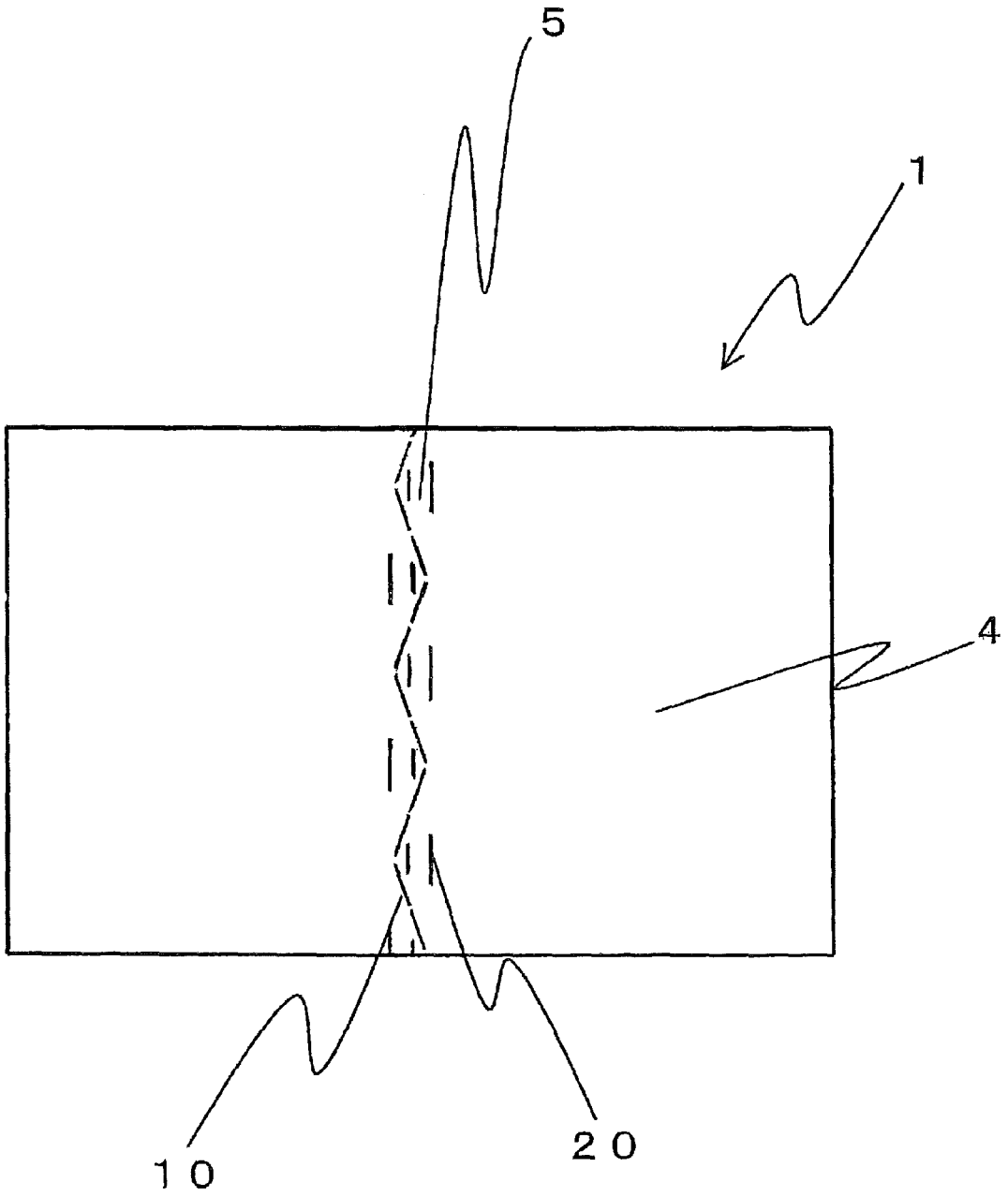
FIG. 9 shows a descriptive drawing (front view) illustrating one embodiment of a patch of the invention.
Figure 10:
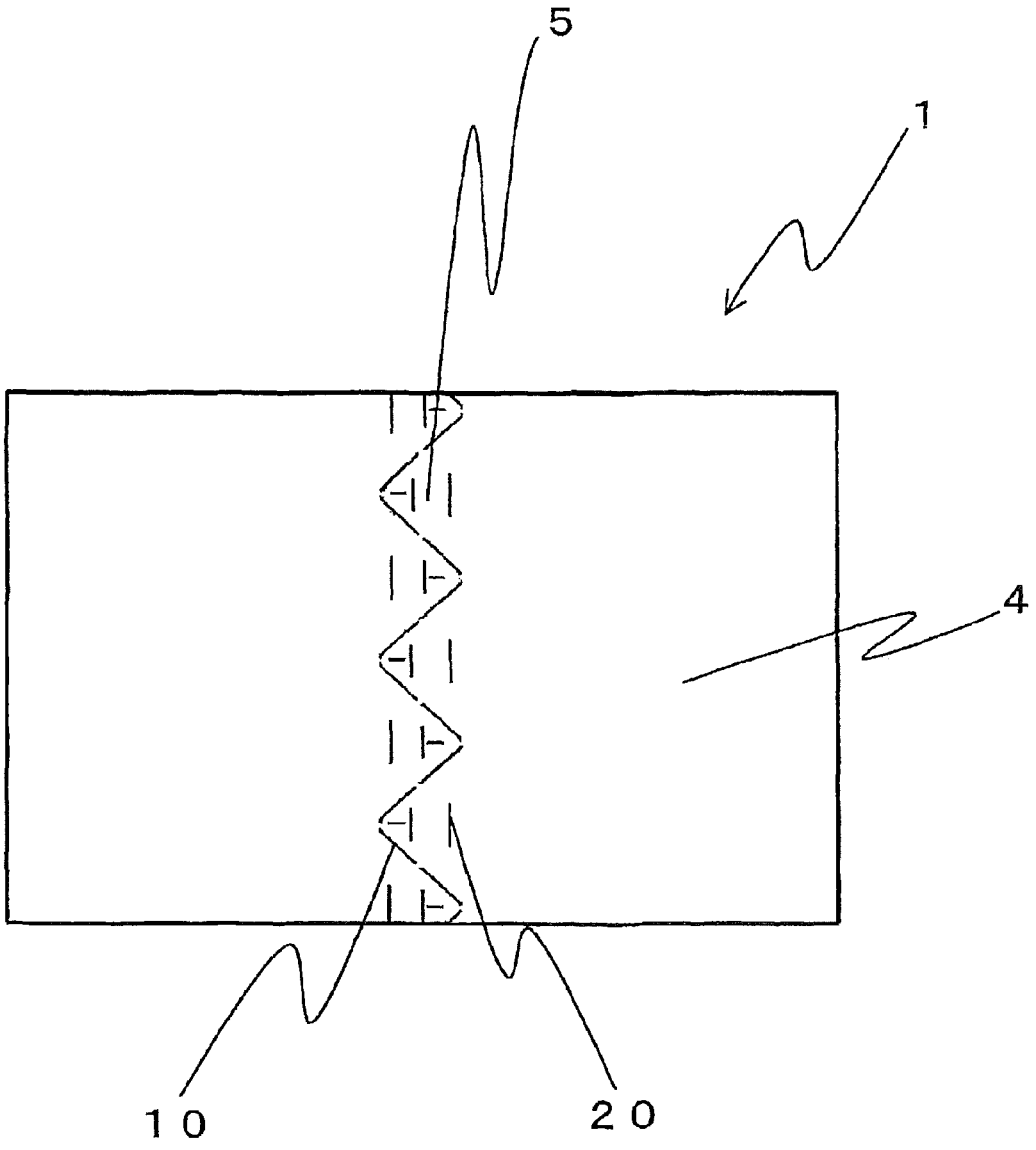
FIG. 10 shows a descriptive drawing (front view) illustrating one embodiment of a patch of the invention.
Figure 11:
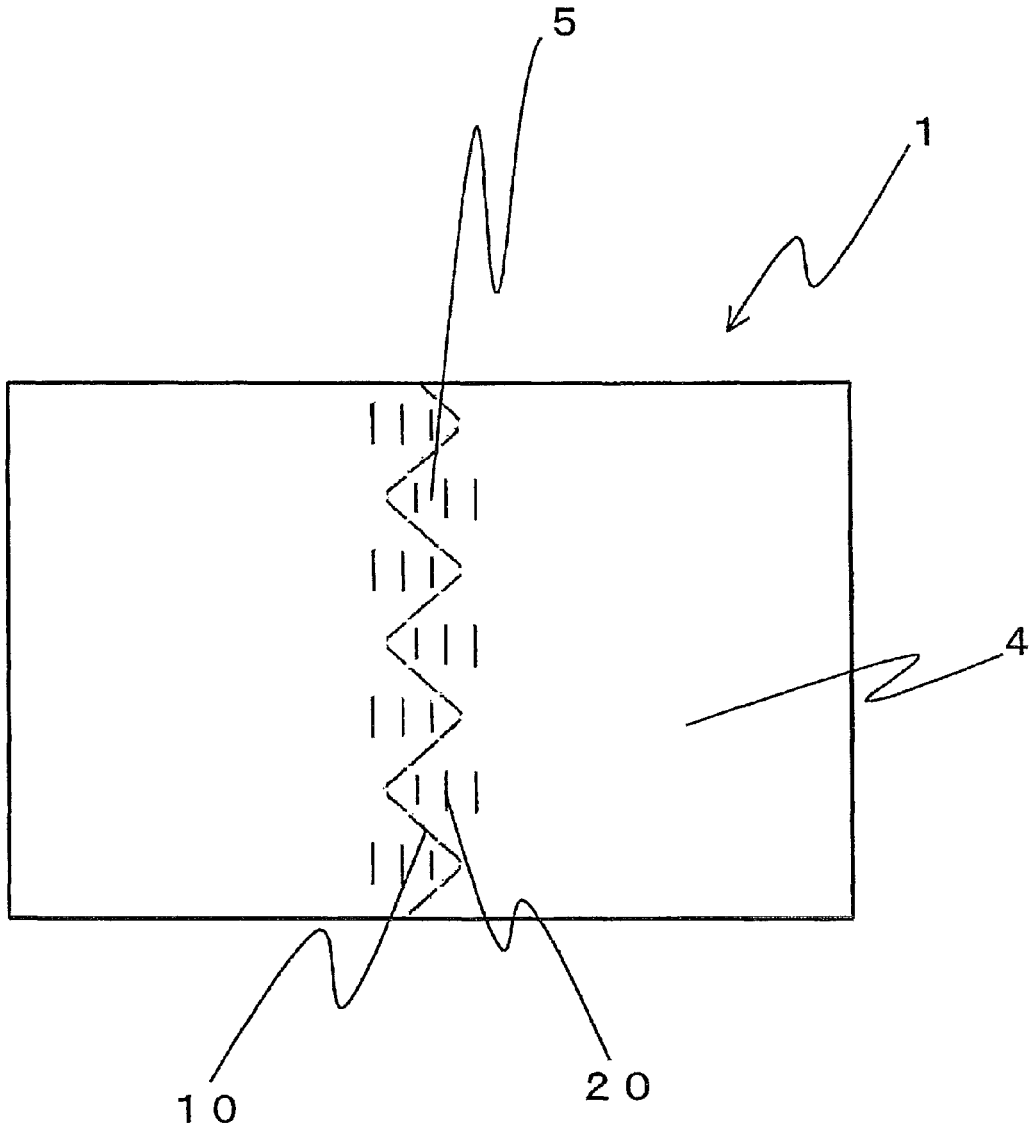
FIG. 11 shows a descriptive drawing (front view) illustrating one embodiment of a patch of the invention.
Figure 12:
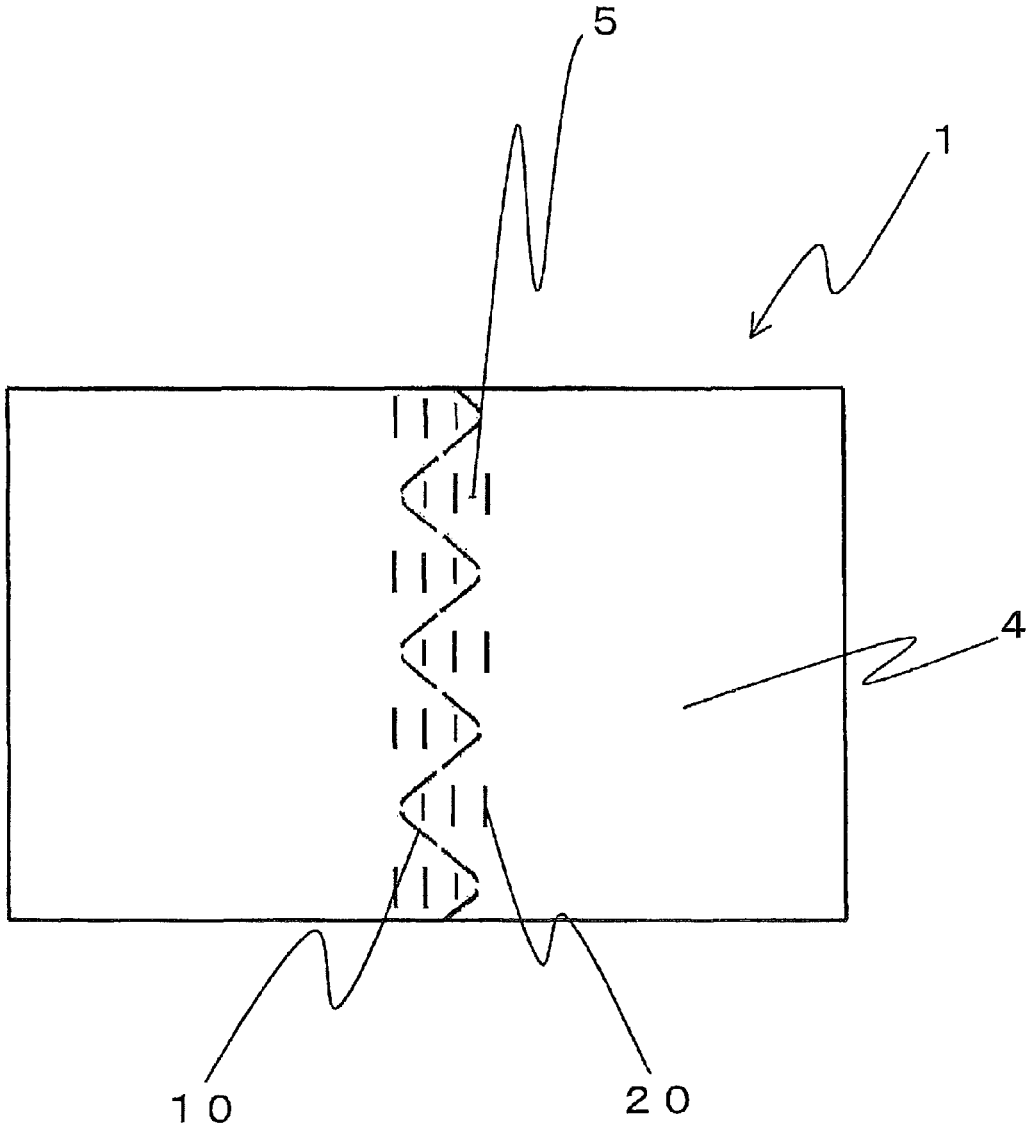
FIG. 12 shows a descriptive drawing (front view) illustrating one embodiment of a patch of the invention.

The patches shown in FIGS. 9-12 illustrate further embodiments. In FIG. 9, the angle of the convex part of the division part 10 is large, while the precut part 20 is provided in one line along the central line of the division zone 10, and another line is additionally provided in the section 5. In FIG. 10, the angle of the convex part of the division part 10 is about 70°-90°, while the precut part 20 comprising two lines parallel and one line vertical to the central line of the division zone 10 is provided in the convex part. In FIGS. 11 and 12, the precut part 20 comprising three lines parallel to the central line of the division zone 10 is provided in the convex part, wherein the embodiment (FIG. 11) has two connections in one ridgeline of the convex part, whereas the embodiment (FIG. 12) has one connection.

Further, the patches shown in FIGS. 13-17 illustrate further embodiments, wherein all or a part of the precut part 20 are provided in the convex pattern toward the outer side (apart directions). With the precut part 20 in such a form, as the patch is pulled away, the tip of the precut part 20 of convex pattern is pulled so as to be caught by the adhesive mass 3, and therefore, the turn-up of the release sheet 4 and exposure of the adhesive mass surface are facilitated, and convenience is further increased.

Figure 13:
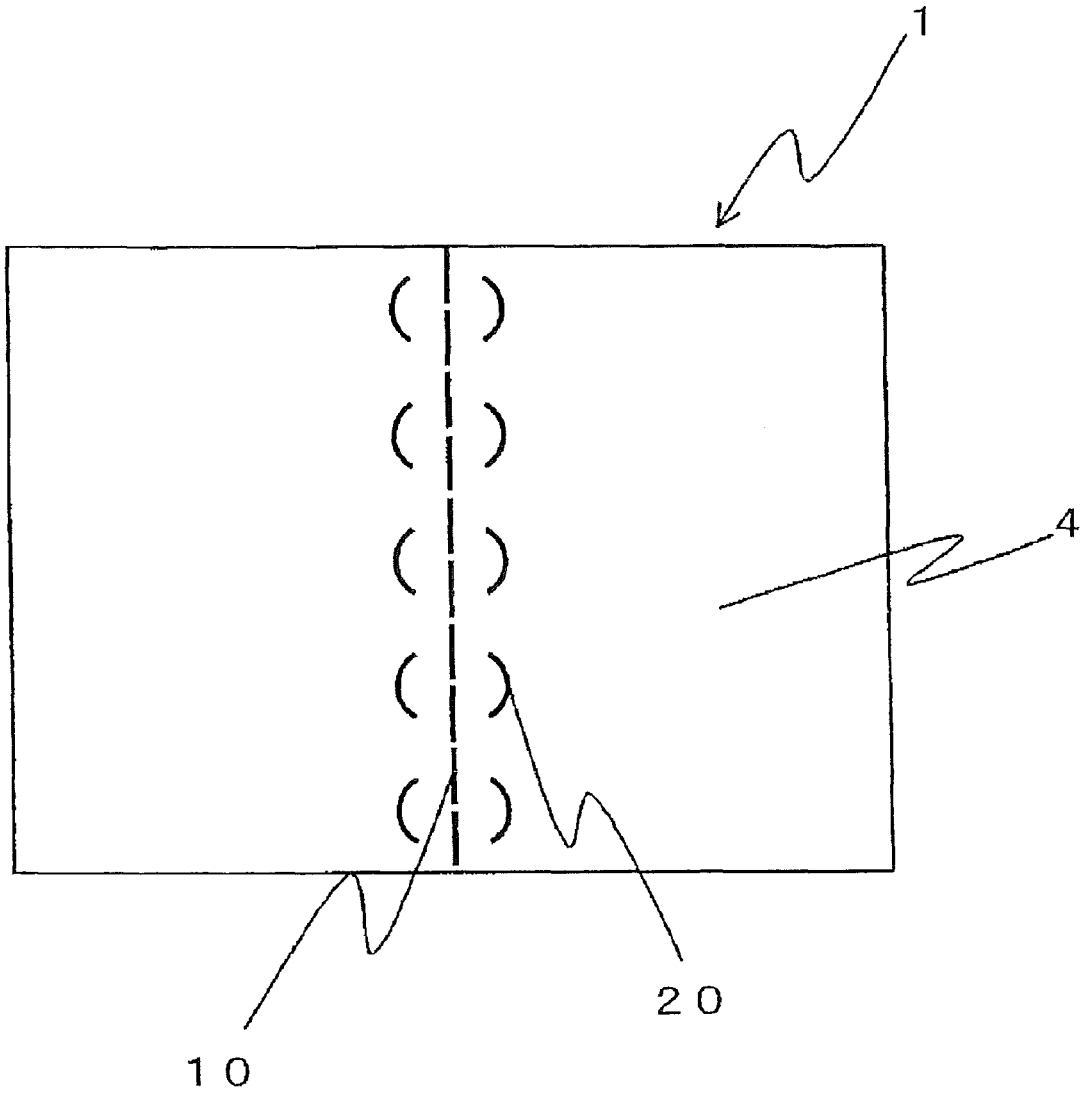
FIG. 13 shows a descriptive drawing (front view) illustrating one embodiment of a patch of the invention.
Figure 14:
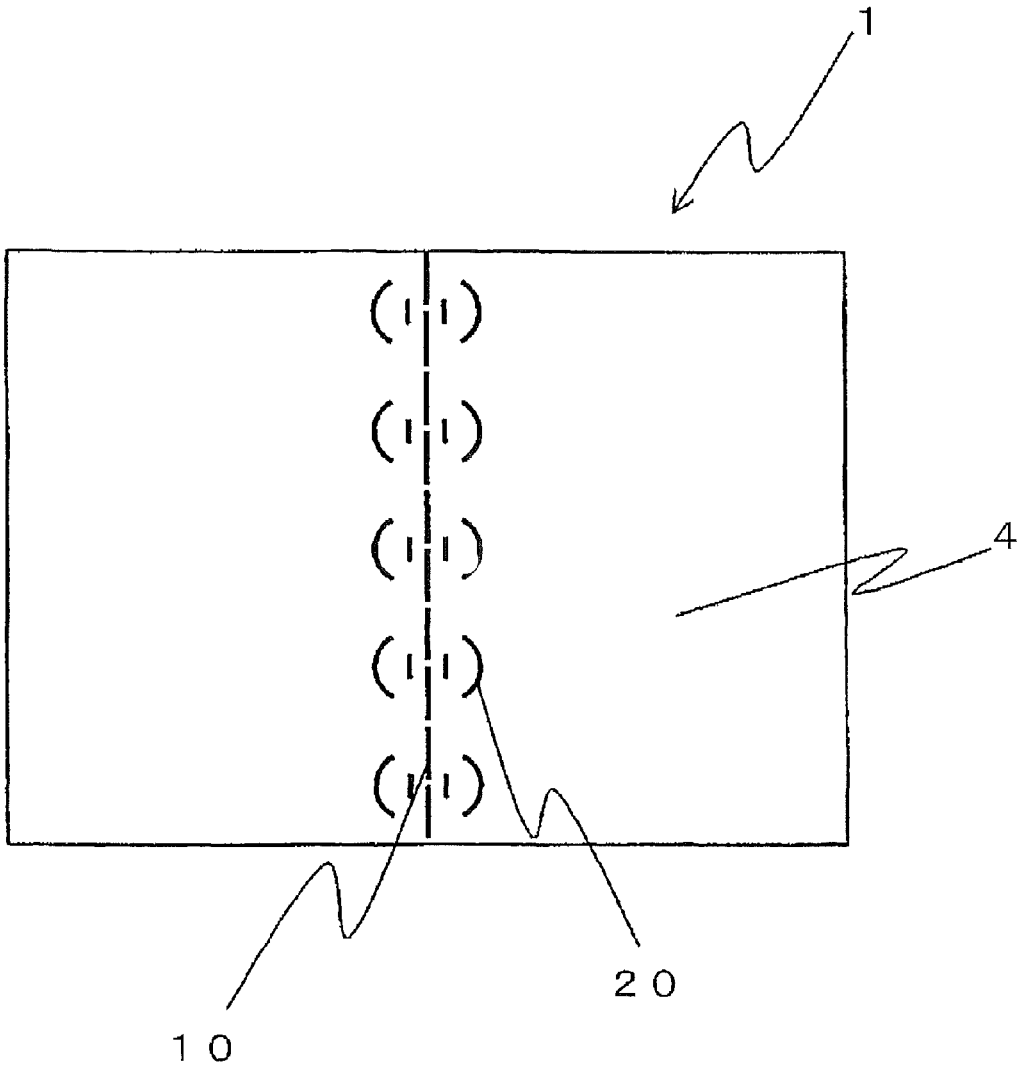
FIG. 14 shows a descriptive drawing (front view) illustrating one embodiment of a patch of the invention.
Figure 15:
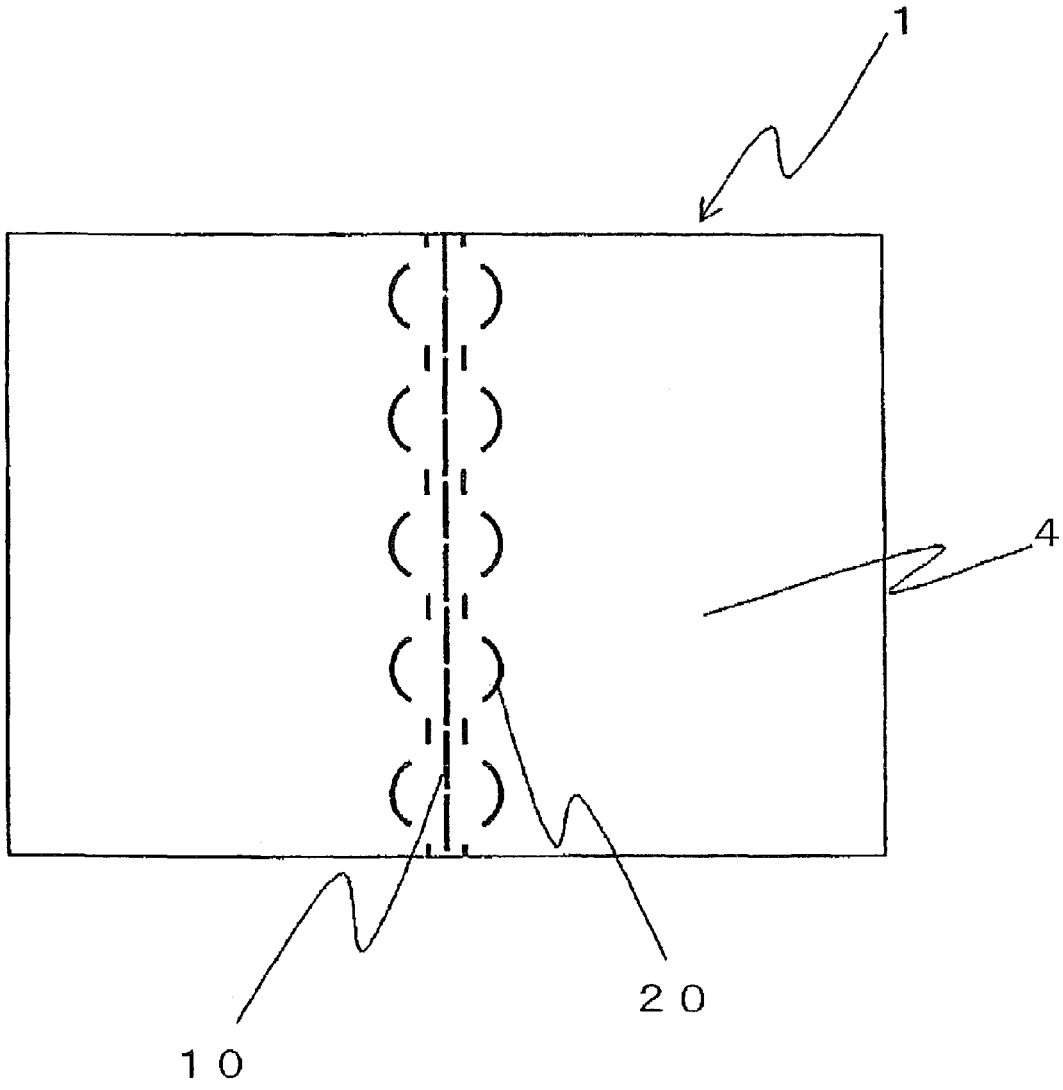
FIG. 15 shows a descriptive drawing (front view) illustrating one embodiment of a patch of the invention.
Figure 16:
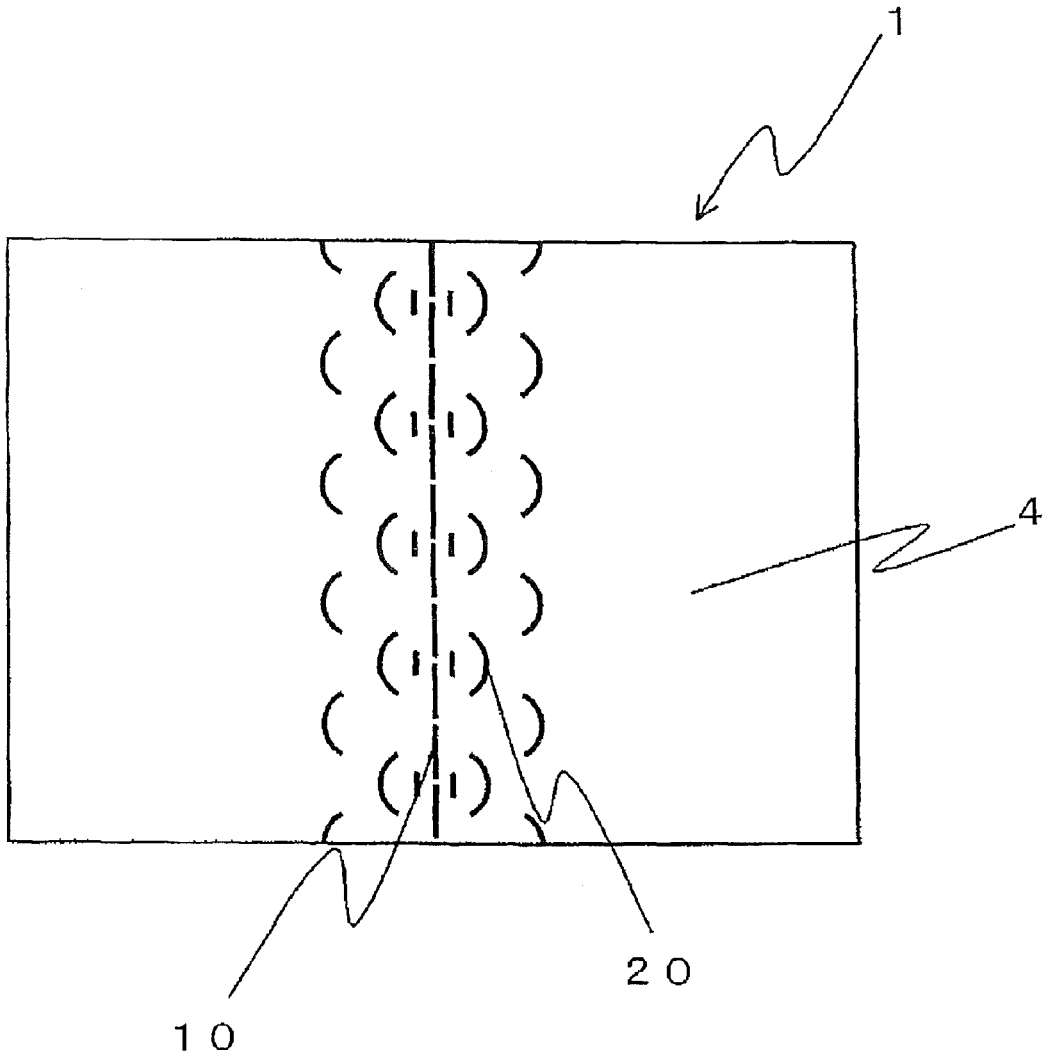
FIG. 16 shows a descriptive drawing (front view) illustrating one embodiment of a patch of the invention.

In FIG. 13, the circular arc precut part 20 is provided in both sides of the division zone 10 in straight line pattern; in FIG. 14, the precut part 20 is further provided in the circular arc, and in FIG. 15, it is provided side by side with the circular arc. In FIG. 16, the circular arc precut part is provided in two lines on one side in the embodiment described in FIG. 14. The length of the circular arc precut part and the radius of its curvature can appropriately be changed.

Figure 17:
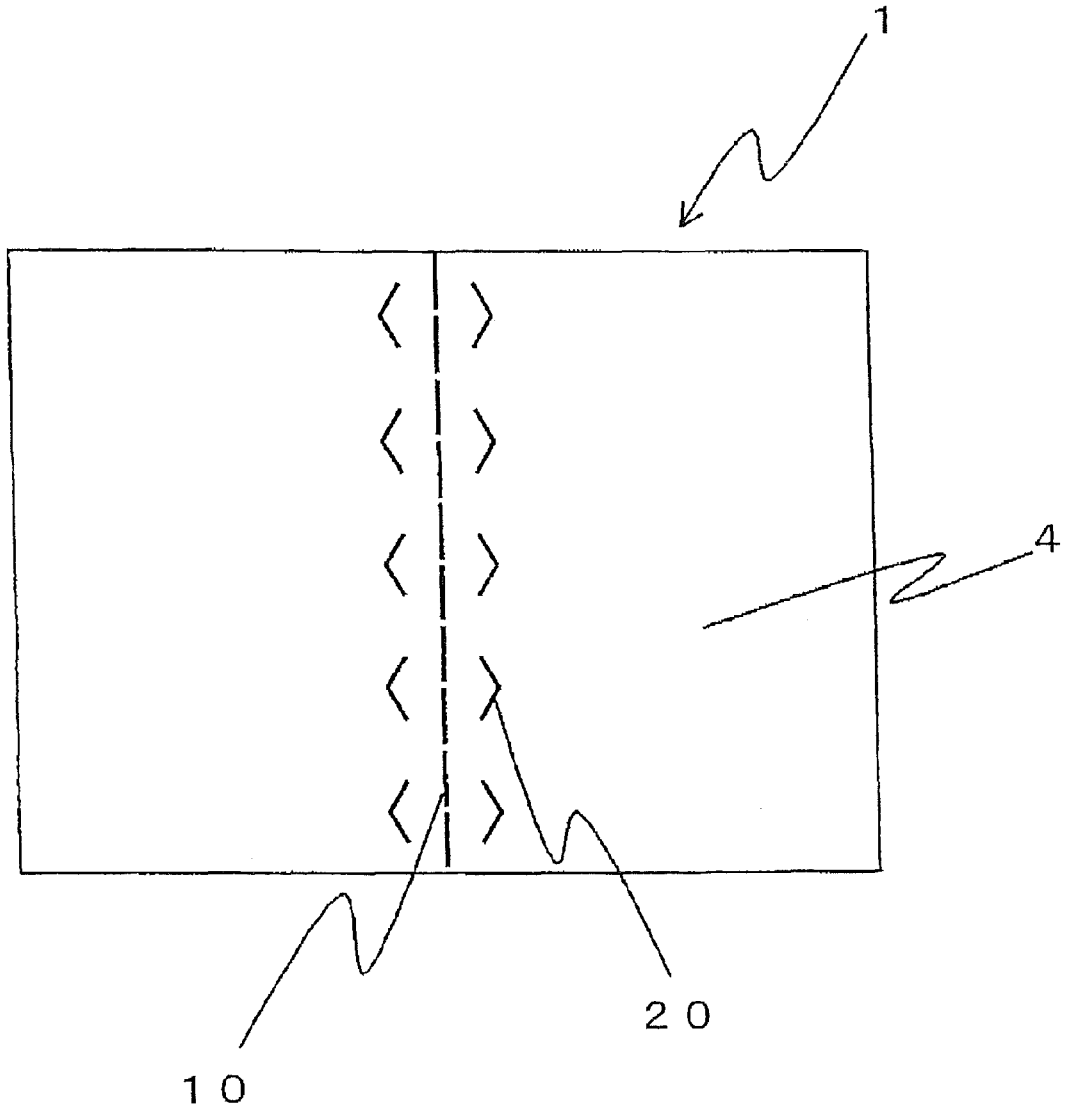
FIG. 17 shows a descriptive drawing (front view) illustrating one embodiment of a patch of the invention.

FIG. 17 shows one embodiment, wherein on both sides of the division zone 10 arranged in straight-line pattern, the V-shaped precut part 20 is provided in the convex pattern toward the pulling directions from the division zone.

It is preferable to make the V-shaped precut part about 3-10 mm away from the division zone, the angle of the V-shape about 40°-70°, the height of the convex of V-shaped pattern about 5-20 mm, and the distance between the V-shapes about 10-30 mm.

EXAMPLE

Example 1

Ten healthy adults of 50-70 years old pulled both ends of the patches having the shape and position of the precut parts as shown in FIGS. 1-3, and the easiness to pick the release sheet and the easiness to stick were evaluated according to the below standard compared with those of the comparative example (those without the precut part in FIG. 1). The mean values of the marking results are shown in Table 1.

TABLE 1

| | FIG. 1 | FIG. 2 | FIG. 3 | Comparative example |
|---|---|---|---|---|
| Easiness to pick release sheet | 2.9 | 2.7 | 2.5 | 1* |
| Easiness to stick | 3.0 | 3.0 | 2.9 | 1* |

*The comparative example was evaluated as 1.
Marks:
Easiness to pick release sheet
3: very easy to pick compared with the comparative example
2: easy to pick compared with the comparative example
1: the same degree as the comparative example
Easiness to stick
3: very easy to stick compared with the comparative example
2: easy to stick compared whit the comparative example
1: the same degree as the comparative example

Example 2

In the release sheet of the patch, the precut part was formed as described in FIG. 17, and the patch was pulled apart to ascertain the turn-up after dividing the release sheet.

The V-shaped precut part 20 was provided at about 5 mm from the division zone 10 in a repetitive pattern. The angle of the V-shape was made 55°; the height of the V-shaped pattern was made 10 mm, and the distance between the V-shapes was made 20 mm.

The turn-up of the release sheet when pulling the patch apart was extremely favorable compared with one without the precut. Further, when the patch is released, the turn-up state was easily maintained.

INDUSTRIAL APPLICABILITY

The invention relates to a patch such as a cataplasm or a plaster and can provide the patch such as the cataplasm or the plaster that are low in cost and apt to mass production, wherein it is possible to easily divide a release sheet by simply pulling the patch such as the cataplasm or the plaster apart, and by simply applying the exposed part of the release sheet to a diseased part, even an aged person can stick it cleanly without unnecessarily touching an adhesive mass and without leaving creases.

The invention claimed is:

1. A patch comprising*:*

(*a*) a stretchable support[,]*;*

(*b*) an adhesive mass laminated substantially all over one surface of the support*;* and (*c*) a release sheet *with:*

(*i*) *a division zone; and*

(*ii*) *one or more precut parts in addition to the division zone positioned near but separate from the division zone;*

*said release sheet being* attached to the entire surface of the adhesive mass*;* wherein only the release sheet *of the patch* is divided at [a] *the* division zone by simply pulling apart *the patch*, and wherein *the* one or more precut parts [that] *in addition to the division zone positioned near but separate from the division zone* are opened when the patch is pulled apart [are provided in the release sheet near the division zone] so that edges of the divided release sheet turn up upon pulling apart to facilitate detachment of the release sheet from the adhesive mass *and to prevent re-sticking of the release sheet*.

2. The patch according to claim 1, wherein the division zone is arranged in an S-shaped pattern, a wavy pattern or a zigzag pattern.

3. The patch according to claim 1, wherein the division zone is arranged in a straight-line pattern.

4. The patch according to claim 1, wherein the division zone is arranged in a T-shaped pattern.

5. The patch according to claim 4, wherein the longitudinal bar of a T-shape is parallel to pulling direction of the patch and the tip of said longitudinal bar is pointed toward the division zone.

6. The patch according to claim 1, wherein the precut part is provided convexly toward the pulling directions from the division zone.

7. The patch according to claim 6, wherein the division zone is arranged in a V-shaped pattern or a circular arc pattern.

8. The patch according to claim 1, wherein the release sheet is one piece of release sheet having a division zone, and only the release sheet is divided at the division zone due to the difference in a rate of elongation between the release sheet and the support by simply pulling the patch apart.

*9. The patch according to claim 1, wherein the precut parts are provided in the form of a T-shaped pattern.*

*10. The patch according to claim 9, wherein the longitudinal bar of a T-shape is parallel to pulling direction of the patch and the tip of said longitudinal bar is pointed toward the division zone.*

*11. The patch according to claim 6, wherein the precut parts are provided in the form of a V-shaped pattern or a circular arc pattern.*

* * * * *